United States Patent [19]
Lane et al.

[11] Patent Number: 5,674,297
[45] Date of Patent: Oct. 7, 1997

[54] METACARPOPHALANGEAL PROSTHESIS

[76] Inventors: Lewis B. Lane, 280 Elderfields, Manhasset, N.Y. 11030; Daniel Edwin Williamson, 2228 S. Stonebridge Rd., Warsaw, Id. 46580

[21] Appl. No.: 569,648

[22] Filed: Dec. 8, 1995

[51] Int. Cl.$^6$ .................................................. A61F 2/42
[52] U.S. Cl. ........................................ 623/18; 623/21
[58] Field of Search .................................. 623/18, 21

[56] References Cited

U.S. PATENT DOCUMENTS

| | | |
|---|---|---|
| 3,837,008 | 9/1974 | Bahler et al. |
| 3,869,729 | 3/1975 | Attenborough |
| 3,899,796 | 8/1975 | Bahler et al. |
| 3,946,445 | 3/1976 | Bentley et al. |
| 3,965,489 | 6/1976 | Freeman et al. |
| 3,990,116 | 11/1976 | Fixel et al. |
| 3,990,118 | 11/1976 | Strickland et al. |
| 3,991,425 | 11/1976 | Martin et al. |
| 3,992,726 | 11/1976 | Freeman et al. |
| 4,003,096 | 1/1977 | Frey |
| 4,011,603 | 3/1977 | Steffee |
| 4,059,854 | 11/1977 | Laure |
| 4,064,568 | 12/1977 | Grundei et al. |
| 4,106,128 | 8/1978 | Greenwald et al. |
| 4,156,296 | 5/1979 | Johnson et al. |
| 4,231,121 | 11/1980 | Lewis |
| 4,242,759 | 1/1981 | White |
| 4,301,552 | 11/1981 | London |
| 4,304,011 | 12/1981 | Whelan, III |
| 4,349,922 | 9/1982 | Agee |
| 4,352,212 | 10/1982 | Greene et al. |
| 4,470,158 | 9/1984 | Pappas et al. |
| 4,634,444 | 1/1987 | Noiles .................... 623/20 |
| 4,642,122 | 2/1987 | Steffee ................... 623/21 |
| 4,645,505 | 2/1987 | Swanson ................. 623/21 |
| 4,725,280 | 2/1988 | Laure ..................... 623/21 |
| 4,731,087 | 3/1988 | Sculco et al. .......... 623/21 |
| 4,759,768 | 7/1988 | Hermann et al. ...... 623/21 |
| 4,911,719 | 3/1990 | Merle ..................... 623/21 |

(List continued on next page.)

FOREIGN PATENT DOCUMENTS

| | | |
|---|---|---|
| 0572339A1 | 1/1993 | European Pat. Off. |
| 2605878A1 | 6/1988 | France |
| 1333412 | 10/1973 | United Kingdom |

OTHER PUBLICATIONS

Beckenbaugh et al, "Total Joint Arthroplasty for the Metacarpophalangeal Joint of the Thumb–A Preliminary Report", *Orthopedics*, Mar. 1981, vol. 4, No. 3, pp. 295–298.

Beckenbaugh et al, "Arthoplasty in the Hand and Wrist", *Operative Hand Surgery*, Third Edition, 1993, vol. 1, pp. 156–159, 183–187.

Gillespie et al, "Biomechanical Evaluation of Metacarpophalangeal Joint Prosthesis Designs", *The Journal of Hand Surgery*, Nov. 1979, vol. 4, No. 6, pp. 508–521.

Doi et al, "Alumina Ceramic Finger Implants: A Preliminary Biomaterial and Clinical Evaluation", *The Journal of Hand Surgery*, American Volume, Sep. 1984, vol. 9A, No. 5, pp. 740–749.

Richards Manufacturing Co., Inc., *Orthopedic Catalog*, 1981.

*Primary Examiner*—Randy C. Shay
*Attorney, Agent, or Firm*—Harness, Dickey & Pierce, P.L.C.

[57] ABSTRACT

A metacarpophalangeal prosthesis includes a metacarpal component having a head portion and a phalangeal component having a socket portion. The head portion rotatably engages the socket portion member. The head portion is either circular or spherical, and the socket portion member is formed so as to cooperate rotatably with the head portion. In its preferred embodiment, a pair of shoulders are formed on the sides of a circular disk-like head portion and a pair of spaced apart surfaces are formed on the socket portion which contact the shoulders of the head portion when the phalangeal component is at maximum flexion. This contact constrains radial and ulnar deviation between maximum flexion and maximum extension such that at maximum flexion radial and ulnar deviation are constrained virtually altogether, while at the neutral position and at maximum extension, limited range of motion and limited radial and ulnar deviation is permitted.

23 Claims, 7 Drawing Sheets

U.S. PATENT DOCUMENTS

| | | | |
|---|---|---|---|
| 4,944,758 | 7/1990 | Bekki et al. | 623/21 |
| 4,955,916 | 9/1990 | Carignan et al. | 623/21 |
| 4,959,071 | 9/1990 | Brown et al. | 623/20 |
| 4,964,861 | 10/1990 | Agee et al. | 606/87 |
| 5,007,932 | 4/1991 | Bekki et al. | 623/21 |
| 5,037,440 | 8/1991 | Koenig | 623/21 |
| 5,047,059 | 9/1991 | Saffar | 623/21 |
| 5,092,896 | 3/1992 | Meuli et al. | 623/21 |
| 5,108,443 | 4/1992 | Branemark | 623/21 |
| 5,147,386 | 9/1992 | Carignan et al. | 623/21 |
| 5,219,362 | 6/1993 | Tuke et al. | 623/20 |
| 5,246,460 | 9/1993 | Goodfellow et al. | 623/20 |
| 5,314,479 | 5/1994 | Rockwood, Jr. et al. | 623/19 |
| 5,405,399 | 4/1995 | Tornier | 623/21 |
| 5,405,400 | 4/1995 | Linscheid et al. | 623/21 |
| 5,405,401 | 4/1995 | Lippincott, III et al. | 623/21 |
| 5,425,777 | 6/1995 | Sarkisian et al. | 623/21 |

METACARPOPHALANGEAL PROSTHESIS

BACKGROUND OF THE INVENTION

1. Field of the Invention

The present invention relates generally to joint prostheses and, more particularly, to a joint prosthesis used to replace the joint between a metacarpal and its associated proximal phalanx. The prosthetic joint alters restraint of radial and ulnar deviation of the phalanx through the range of motion of the finger and mimics the movement of the replaced natural joint. Furthermore, the joint of the present invention provides additional constraint in a joint compromised by disease including the loss of soft tissue.

2. Description of the Relevant Art

The metacarpophalangeal joint is occasionally affected by certain problems such as rheumatoid arthritis and post-traumatic osteoarthrosis. Either condition can be mildly debilitating or, in extreme cases, can lead to loss of function and pain of the metacarpophalangeal joint. Replacement of the metacarpophalangeal joint using a prosthetic joint is often necessary in the latter case.

Prosthetic replacements for the metacarpophalangeal joint have been known in various designs for over half a century. Early versions of these prosthetics included a metacarpal portion and a phalangeal portion hinged together by a pin. Both portions were composed of metal. These early designs limited movement of the finger to flexion and extension only. Later versions of the metacarpophalangeal prosthetic were composed of flexible, polymerized materials and allowed, in addition to flexion and extension, radial and ulnar deviation.

While providing some relief to persons suffering from metacarpophalangeal joint destruction, these early prosthetics do not provide completely natural movement. Attempts have been made to overcome this problem. For example, in U.S. Pat. No. 5,007,932, an artificial joint is disclosed having concave and curved surfaces which provide for a sliding connection. In U.S. Pat. No. 5,405,401, a joint prosthesis is disclosed which is intended to limit lateral pivoting of one bone with respect to the other bone when the bones are flexed through a predetermined angle.

However, these improvements nevertheless do not provide a prosthetic joint that completely mimics the movement and function of the replaced natural joint. In particular, known joints either do not adequately constrain radial and ulnar deviation by differing degrees between flexion and extension or do not adequately transfer load between the metacarpal component and the phalangeal component continuously and completely during the full range of finger motion.

SUMMARY OF THE INVENTION

The present invention overcomes the deficiencies of known metacarpophalangeal prosthetic devices by providing mated metacarpal and phalangeal components that provide adequate constraint and articulation to allow function without pain similar to the natural metacarpophalangeal joint. The present invention includes a metacarpal component having a head portion and a phalangeal component having a socket portion member. The head portion rotatably engages the socket portion member. The head portion may be either circular (and disk-like) or spherical, and the socket portion member is formed so as to rotatably cooperate with the head portion.

Radial and ulnar deviation is constrained by structures formed on the metacarpal component and on the phalangeal component. In a first preferred embodiment that incorporates the circular, disk-like head portion and a cooperating socket portion member, a pair of shoulders are formed on the sides of the circular head portion. The shoulders have upper and lower surfaces. The socket portion member has a pair of spaced apart surfaces that intimately contact the shoulders associated with the head portion when the phalangeal component is at maximum flexion or at maximum radial-ulnar deviation through the remaining range of motion.

When at maximum flexion, contact between the shoulders and the spaced apart surfaces restricts radial and ulnar deviation entirely, while contact between the shoulders and the spaced apart surfaces as well as the head and socket portion allow a limited amount of radial-ulnar deviation throughout the remaining range of motion. Such deviation is also permitted at the neutral position. The surfaces and shoulders are formed such that as the phalangeal component is moved from the neutral position to maximum flexion, radial and ulnar deviation becomes increasingly constrained until prohibited entirely when maximum flexion is reached.

Accordingly, it is an object of the present invention to provide a metacarpophalangeal prosthesis which allows both maximum flexion and maximum extension to degrees which approximate those capable in a natural joint.

It is an additional object of the present invention to provide such a prosthesis which constrains radial and ulnar deviation between maximum flexion and maximum extension such that at maximum flexion, radial and ulnar deviation is constrained substantially altogether, while at the neutral position and at maximum extension, radial and ulnar deviation is permitted.

Still a further object of the present invention is to provide a prosthesis which increasingly constrains radial and ulnar deviation as the phalangeal component is moved from the neutral position to maximum flexion until such deviation is substantially prohibited entirely.

Yet an additional object of the present invention is to provide such a prosthesis in which the components or the articulating surfaces of the components are composed of different materials, whereby friction is minimized.

It is another object of the present invention to provide a prosthesis in which the load is primarily shared between the head portion of the metacarpal component and the socket portion member of the phalangeal component continuously through the range of motion between maximum flexion and maximum extension.

Still a further object of the present invention is to provide such a prosthetic which does not utilize connectors or fasteners between the metacarpal component and the phalangeal component.

An additional object of the present invention is to provide such a prosthetic which comprises two separable components, each of which being capable of being installed independent of the other.

Yet a further object of the present invention is to provide such a prosthetic device having an axis of rotation that is offset from the centerline of the metacarpophalangeal joint.

A further object of the present invention is to provide such a device which allows for up to 90 degrees of flexion or about 45 degrees of hyperextension.

Still a further object of the present invention is to provide such a prosthetic which includes spherical and smooth surfaces to minimize damage to tendons and ligaments.

Yet an additional object of the present invention is to provide such a prosthetic implant which has axial rotation constraint.

BRIEF DESCRIPTION OF THE DRAWINGS

The present invention will be more fully understood by reference to the following detailed description of the preferred embodiments of the present invention when read in conjunction with the accompanying drawings, in which like reference characters refer to like parts throughout the views, and in which.

DETAILED DESCRIPTION OF THE PREFERRED EMBODIMENT

The drawings disclose the preferred embodiment of the present invention. While the configurations according to the illustrated embodiment are preferred, it is envisioned that alternate configurations of the present invention may be adopted without deviating from the invention as portrayed.

Figure 1:
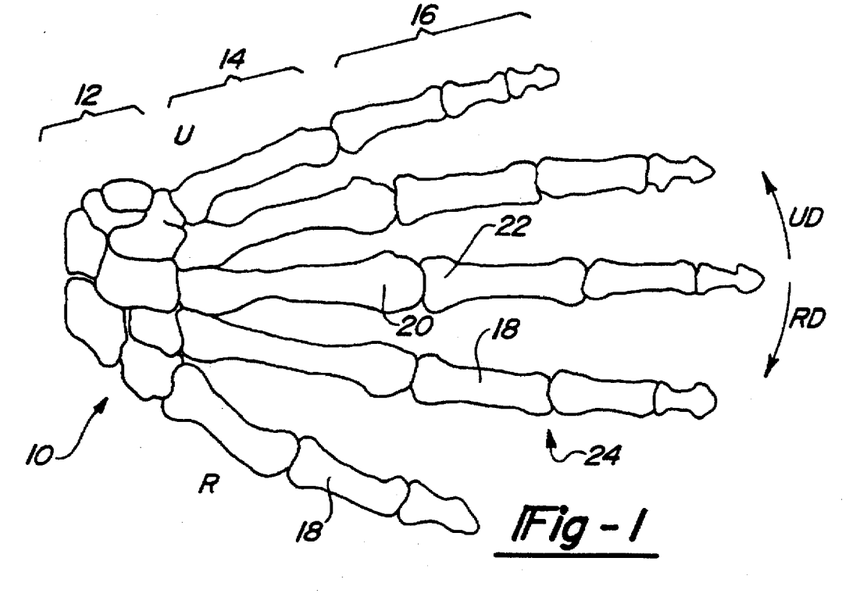
FIG. 1 is a top view of the bones of the left wrist and hand.

Referring to FIG. 1, a top plan or posterior view of the bones of a left hand are generally illustrated as 10 and include a radial side ("R") and an ulnar side ("U"). The hand 10 include the carpals 12, the metacarpals 14, and the phalanges 16. The phalanges 16 include proximal phalanges 18. Each of the metacarpals 14 includes a head portion 20 hingedly mated to a socket portion 22 of the phalanges 18. The interaction of the head portion 20 of the metacarpals 14 and the socket portion 22 of the phalanges 18 allow a certain amount of movement of the phalanges 18 with respect to the metacarpals 14. In this regard, when the finger 24 is in its neutral and relaxed position, the head portion 20 and the socket portion 22 permit the finger 24 to have approximately 15 degrees of radial deviation ("RD") and approximately 15 degrees of ulnar deviation ("UD").

Figure 2:
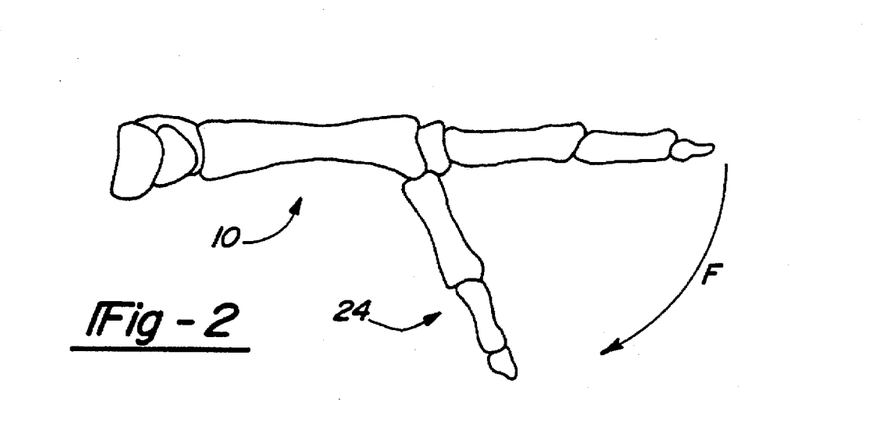
FIG. 2 is a radial side elevational view of the bones of the left wrist and hand illustrating a finger positioned to about 80° of flexion.
Figure 3:
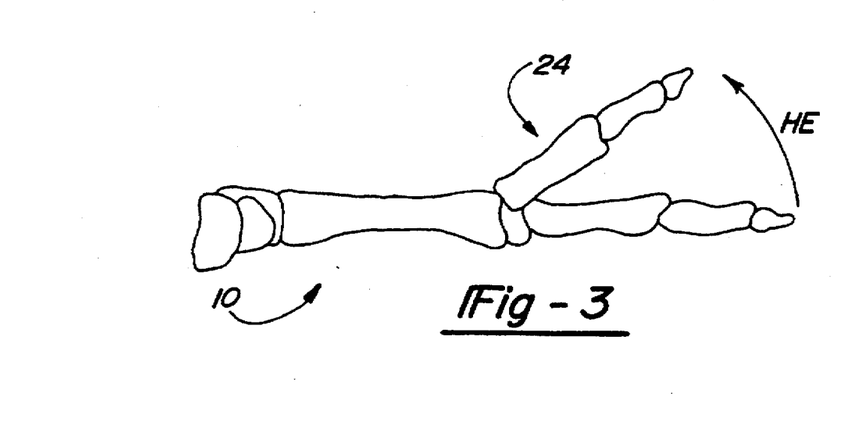
FIG. 3 is a view of the bones of the left wrist and hand similar to that of FIG. 2 illustrating a finger positioned to about 45° of hyperextension.
Figure 3A:
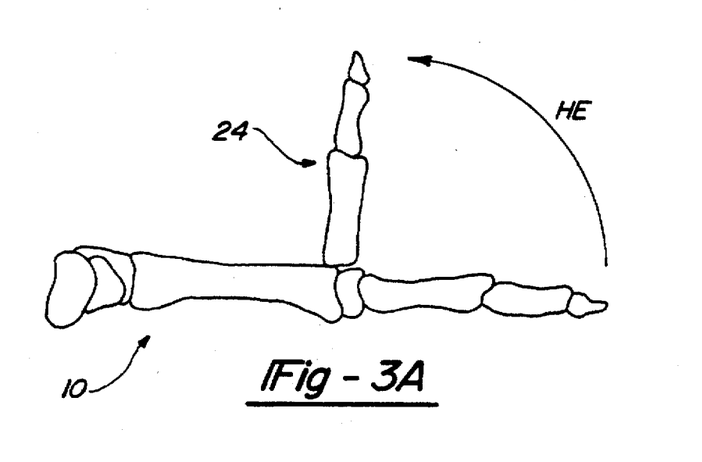
FIG. 3A is a view of the bones of the left wrist and hand similar to that of FIG. 3 but illustrating a finger positioned at about 90° of hyperextension.

As will be appreciated by those skilled in the art, the amount of radial deviation and ulnar deviation in the natural joint will vary depending upon the degree of the flexion of the joint. As shown in FIG. 2 in which a radial side elevational view of the bones of the left wrist and hand are illustrated, the natural metacarpophalangeal joint permits virtually no radial and ulnar deviation when the joint is at maximum flexion of approximately 90 degrees. In contrast, when the natural metacarpophalangeal joint is at hyperextension of approximately 45 degrees as shown in FIG. 3 (a view similar to that of FIG. 2 but illustrating a finger positioned to about 45 degrees of extension), the radial and ulnar deviation permitted by the joint is approximately 15 degrees with the actual magnitude being dependent upon individual physiology. The natural metacarpophalangeal joint may be hyperextended to approximately 90 degrees as illustrated in FIG. 3A. The extreme position illustrated may be achieved when the finger is pressed against a fixed object such as a tabletop.

Referring now to FIGS. 4 through 14, the first preferred embodiment of the present invention is shown. The first preferred embodiment of the present invention includes a metacarpophalangeal prosthesis generally designed by the numeral 30. The metacarpophalangeal prosthesis 30 permits radial and ulnar deviation to approximately 15 degrees when the finger is in its neutral position or when the finger is in extension. However, the metacarpophalangeal component 30 restricts radial and ulnar deviation to approximately 0 degrees when the finger is in a position of maximum flexion. The metacarpophalangeal prosthesis 30 also imitates the natural joint by increasing restriction of radial and ulnar deviation as the finger is moved from its neutral position to maximum flexion. In this regard, radial and ulnar deviation is restricted to approximately 2 degrees when the finger is at 80 degrees of flexion, to approximately 3 degrees when the finger is at 70 degrees of flexion, and to approximately 5 degrees when the finger is at 60 degrees of flexion. Additionally, rotation of said metacarpal component about its longitudinal axis is prohibited with respect to the phalangeal component.

The metacarpophalangeal prosthesis 30 of the present invention will now be described in greater detail. As illustrated generally in the side view of the prosthesis 30 in FIG. 4 and the top view of the prosthesis 30 in FIG. 5, the metacarpophalangeal prosthesis 30 includes a metacarpal component 50 and a phalangeal component 64. The metacarpal component 50 of the metacarpophalangeal prosthesis 30 includes a stem portion 52 and a head portion 54 which are preferably integrally formed from a single material. The stem portion 52 serves as an anchor for attaching the metacarpal component 50 to a surgically prepared metacarpal as is known in the art. The stem portion 52 and head portion 54 are preferably formed from a biocompatible and corrosion-resistant metal such as Ti-6A1-4V, cobalt chrome, or any other suitable material. The head portion 54 is finished to a high degree of smoothness, while the stem portion 52 is preferably finished by sand or other blasting or with a coating such that a porous surface is achieved so as to provide a surface for frictional engagement and subsequent bone ingrowth with the metacarpal 14.

Figure 6:
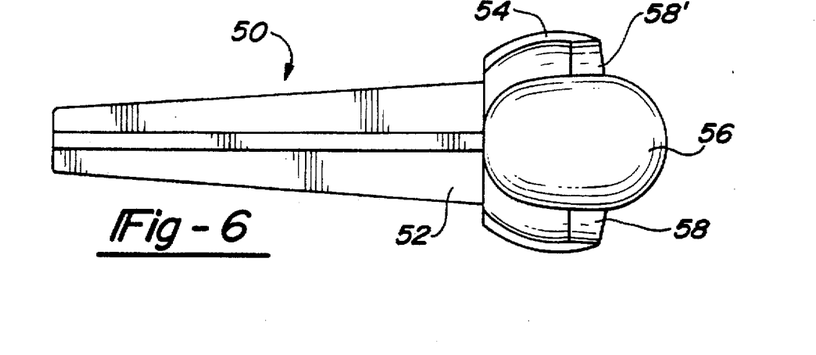
FIG. 6 is a top view of the metacarpal component of the metacarpophalangeal prosthesis of FIGS. 4 and 5.

The head portion 54 of the metacarpophalangeal prosthesis 30 includes a head component 56 and a pair of adjacent shoulders 58 and 58'. The head component 56 is a substantially circular disk-like component having slightly flattened sides as shown in FIG. 6. The shoulder 58 and 58' are similarly constructed and include a substantially planar lower surface 60 and a generally tapered upper surface 62.

Figures 7, 8, 9, 10:
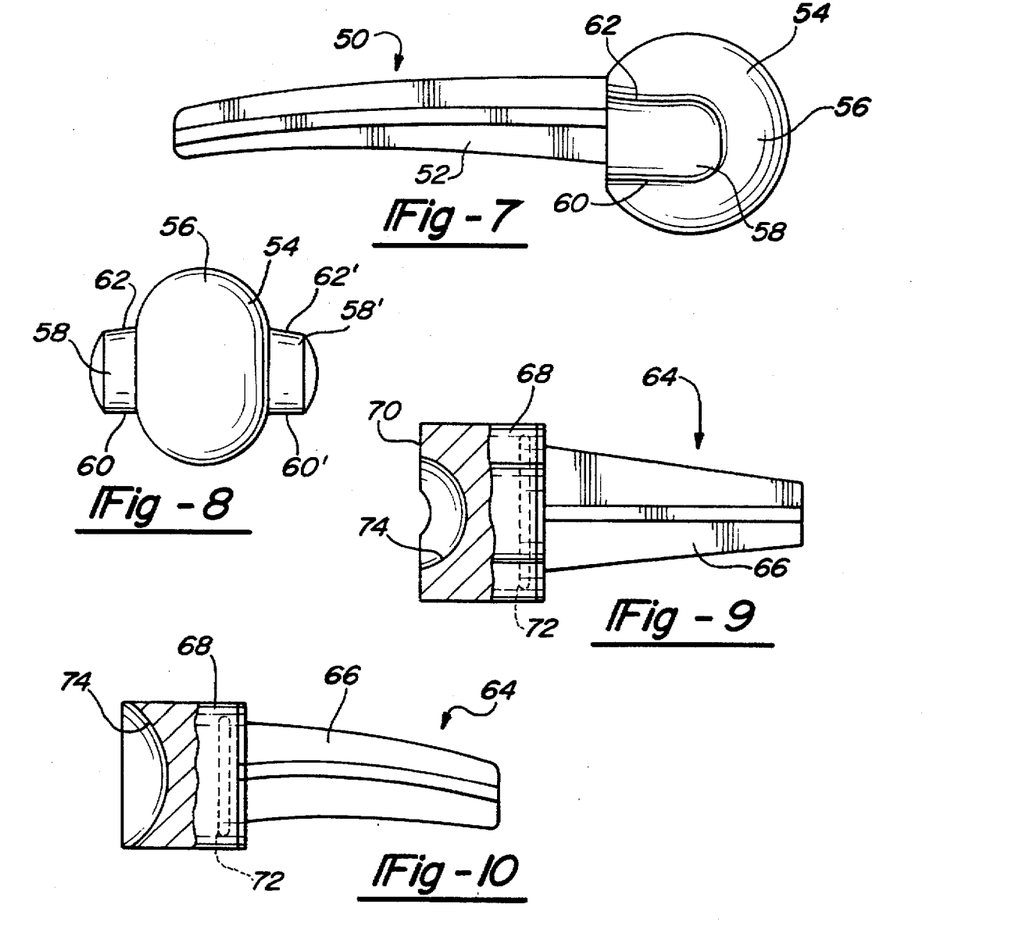
FIG. 7 is a side elevational view of the metacarpal component shown in FIG. 6 according to the teachings of a preferred embodiment of the present invention.
FIG. 8 is an end view of the metacarpal component shown in FIG. 6 according to the teachings of a preferred embodiment of the present invention.
FIG. 9 is a top view of the phalangeal component of the metacarpophalangeal prosthesis according to the teachings of a preferred embodiment of the present invention.
FIG. 10 is a side view of the phalangeal component shown in FIG. 9 according to the teachings of a preferred embodiment of the present invention.

As illustrated in FIG. 6 which is a top view of the metacarpal component 50, FIG. 7 which is a side view of the metacarpal component 50, and FIG. 8 which is an end view of the metacarpal component 50, the lower surface 60 of the shoulder 58 is substantially coplanar with a lower surface 60' of the shoulder 58'. The upper surface 62 of the shoulder 58 has a slight taper with respect to the plane of the lower surface 60. In a similar fashion, the upper surface 62' of the shoulder 58' has a slight taper in the opposite direction of the upper surface 62 with respect to the plane of the lower surface 60'.

The phalangeal component 64 of the metacarpophalangeal prosthesis 30 will now be described in greater detail. As shown in FIGS. 9 and 10 which are top and side views of the phalangeal component respectively, the phalangeal component 64 rotatably mates with the metacarpal component 50 so as to control the amount of radial and ulnar deviation in response to the amount of flexion of the joints. The phalangeal component 64 includes a stem portion 66 and a socket portion 68. As shown in FIGS. 9 and 10, the socket portion 68 of the phalangeal component 64 is molded onto an extension 72 (shown in broken lines) of the stem portion 66. Accordingly, the socket portion 68 may be formed separately from the stem portion 66 and then subsequently attached before the phalangeal component 64 is implanted. This permits the socket portion 68 to be formed from a different material from the stem portion 68 which may be definable under certain circumstances. However, while the phalangeal component 64 has been described above as being composed of a metal or the combination of a metal and a plastic, the phalangeal component 64 may alternatively be composed entirely of a polymerized material such as polyethylene. If formed from a plastic, the phalangeal component 64 may be machined from a solid block or may be molded according to known molding techniques.

The socket portion 68 includes a recessed area 74 which is formed so as to be able to mate with the head component 56 of the metacarpal component 50. The recessed area 74 is clearly seen in FIG. 9 as being a partially fragmented view taken along lines 9—9 of FIG. 11 which is an end view of the phalangeal component 64 and in FIG. 10 as being a partially fragmented view taken along lines 10—10 of FIG. 11. Disposed on the sides of the recess area 74 are a pair of spaced-apart elevated surfaces 76 and 76'. The elevated surfaces 76 and 76' contact portions of the shoulders 58 and 58' respectively at certain positions through the range of flexion as will be discussed more fully below.

Figure 4:
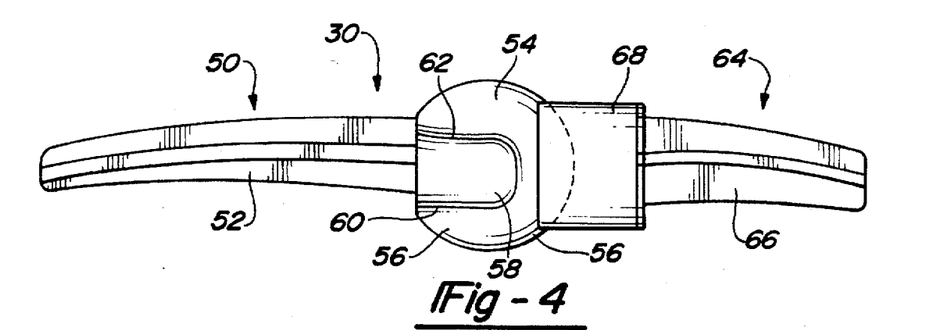
FIG. 4 is a side view of a metacarpophalangeal prosthesis according to the teachings of a preferred embodiment of the present invention.

FIGS. 4, 7, and 10 are side views of the components 50 and 64, either alone or in combination. As illustrated, the stem portions 52 and 66 are formed to define a slight arc of curvature. Alternatively, the stems of the prosthesis according to the present invention could be straight, as illustrated in the embodiments of FIGS. 15 through 29.

Figures 11, 12, 13, 14:
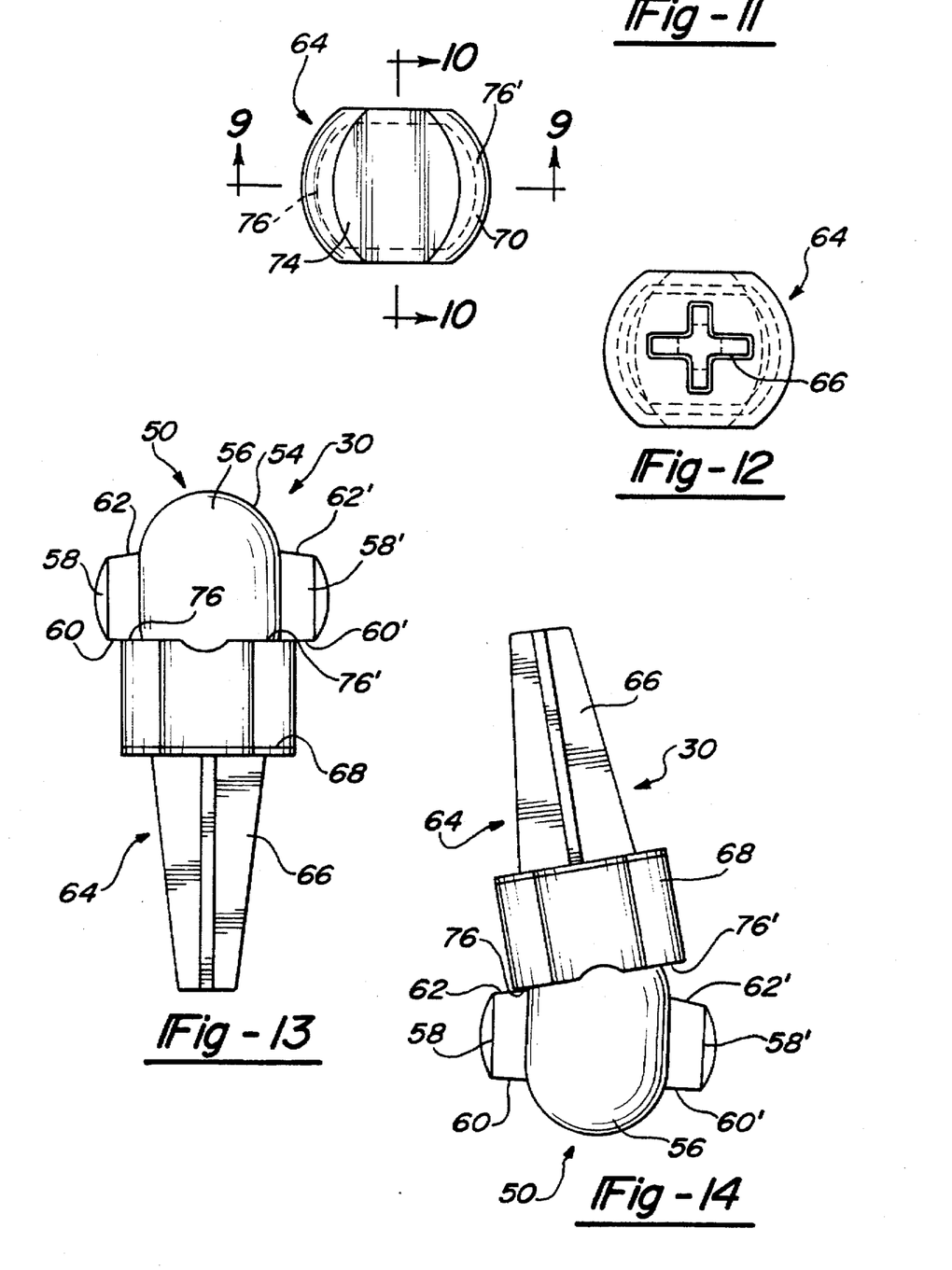
FIG. 11 is an end view of the phalangeal component shown in FIG. 9 according to the teachings of a preferred embodiment of the present invention.
FIG. 12 is an end view of the phalangeal component shown in FIG. 9 according to the teachings of a preferred embodiment of the present invention.
FIG. 13 is a view of the metacarpophalangeal prosthesis according to the teachings of a preferred embodiment of the present invention shown in FIGS. 4 and 5 illustrating the flexion position.
FIG. 14 is a view of the metacarpophalangeal prosthesis according to the teachings of a preferred embodiment of the present invention shown in FIGS. 4 and 5 illustrating the hyperextension position.

The stem portion 66 of the phalangeal component 64 has a cross-section which is cross-shaped as is shown in FIG. 12 taken from the end of the phalangeal component 64 opposite the view of FIG. 11. This construction, which has been adopted for each of the stem portions illustrated and discussed herein, inhibits rotation of the stem portion 66 within the phalange 18. In addition, the cross-sectional configuration of the stem portion 66 maximizes the bone-contacting surface area while simultaneously providing the stem portion 66 with maximum structural integrity. Initially, the cross-shaped construction of the stem portion 66 gives the surgeon information regarding the rotational positioning of the phalangeal component 64 by allowing the surgeon to compare the orientation of the flanges forming the cross-section with vertical. It is to be understood, however, that alternate shapes of the stem portions incorporated into the several components of the various embodiments of the present invention could also be employed without deviating from the general concept of the present invention. The surface finish of the stem portion 66 is preferably the same as that of the stem portion 52 of the metacarpal component 50.

As best shown in FIG. 12, but as may also be understood by reference to FIGS. 4, 7, and 10, the stem 52 is off-center with respect to the head portion 54 and the stem 66 is offset with respect to the socket portion 68. This configuration lowers the center of axis of rotation and positions the center of the axis of rotation in a more palmar position relative to the respective stems.

Figure 5:
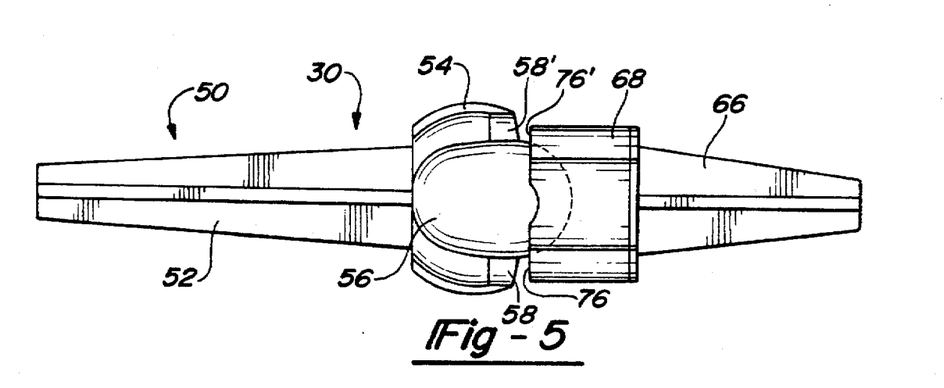
FIG. 5 is a top view of the metacarpophalangeal prosthesis of FIG. 4.

The operation of the metacarpophalangeal prosthesis 30 will now be described. With respect to the neutral position as shown in FIGS. 4 and 5, the recessed area 74 of the phalangeal component 64 is in full contact with the head component 56 of the metacarpal component 50, while the shoulder 58 is spaced apart from the surface 76 and the shoulder 58' is spaced apart from the surface 76'. Accordingly, the metacarpophalangeal prosthesis 30 permits a limited amount of ulnar and radial deviation. When the finger is moved to full flexion as illustrated in FIG. 13, the lower surface 60 of the shoulder 58 is in virtually full contact with the surface 76 of the socket portion 68 and the lower surface 60' of the shoulder 58' is in virtually full contact with the surface 76'. This contact prevents ulnar and radial deviation of the phalangeal component 64 with respect to the metacarpal component 50. As the phalangeal component 64 is moved away from full flexion toward the neutral position, the distance between the lower surface 60 and the surface 76 gradually increases as does the distance between the lower surface 60' and the surface 76'. This allows for ulnar and radial deviation that incrementally increases from 0 in full flexion to approximately 15 degrees in the neutral position.

When the finger is moved to its position of maximum extension, the metacarpophalangeal prosthesis 30 permits a limited amount of ulnar and radial deviation. For example, when the phalangeal component 64 is in its position of maximum extension and the finger (not shown) is deviated radially as shown in FIG. 14, the substantially full contact between the surface 76 and the tapered upper surface 62 prevents further radial movement. Similarly, a certain amount of ulnar deviation is permitted before being halted by contact of the surface 76' with the tapered upper surface 62'.

Figure 15:
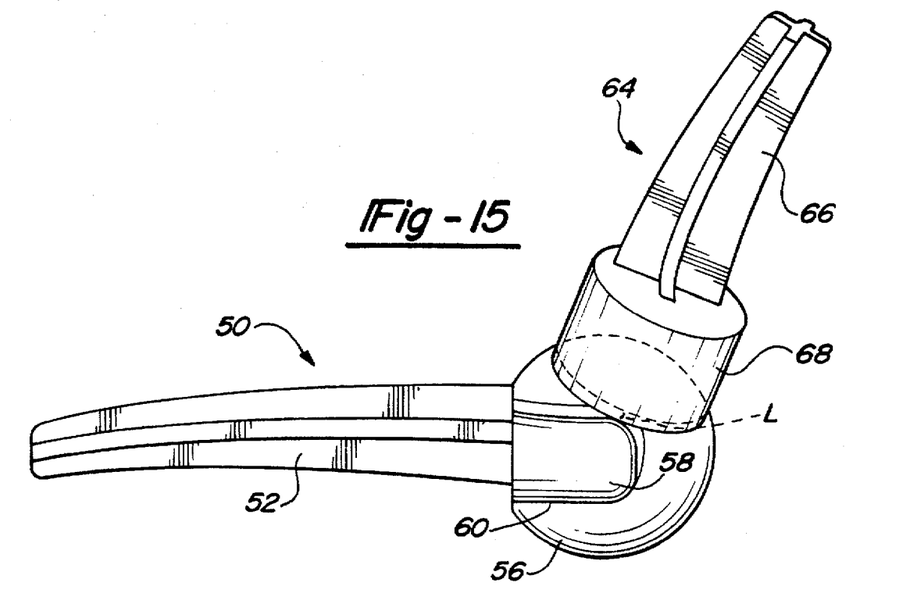
FIG. 15 is a side elevational view of the metacarpophalangeal prothesis according to the teachings of the embodiment of FIG. 14 illustrating the phalangeal component positioned at approximately 45° of hyperextension with respect to the metacarpal component.

Contact also occurs between the surfaces of the shoulders 58 and 58' and the surfaces 76 or 76' when the finger is moved to a position of less than maximum extension as illustrated in FIG. 15 where the phalangeal component 64 is approximately at a 45° angle with respect to the metacarpal component 50. Radial movement is limited by line contact (illustrated by the line "L") between the shoulder 58 (or 58') and the surface 76 (or 76'). The line contact as illustrated in FIG. 15 or the full contact as illustrated in FIG. 14 both provide for a prosthetic joint demonstrating superior resistance to wear.

At all times throughout the range of motion of the metacarpophalangeal prosthesis 30, the head component 56 of the metacarpal component 50 is in contact with the socket portion 68 of the phalangeal component 64, thus transferring the load primarily between the socket portion 68 and the head component 56. Conversely, the shoulders 58 and 58' of the metacarpal component 50 and the surfaces 76 and 76' of the phalangeal component 64 serve to restrict movement and do not provide primary load transfer between the metacarpal component 50 and the phalangeal component 64. This load transferring relationship is an improvement over other metacarpophalangeal prosthetic devices in that it provides superior load-bearing capacity on the main portion of the joint throughout the range of motion, thus decreasing contact stress produced on the elevated surfaces 76 and 76'.

Figure 16:
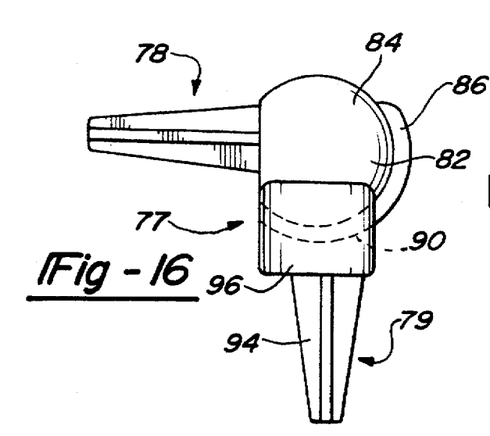
FIG. 16 is a side elevational view of a metacarpophalangeal prosthesis according to an alternate preferred embodiment of the present invention illustrating the components at approximately 90 degrees with respect to each other.

The second preferred embodiment of the metacarpophalangeal prosthesis of the present invention is shown in FIGS. 16 through 20 and will now be described. Referring to FIG. 16, a metacarpophalangeal prosthesis 77 is shown in full flexion and includes a metacarpal component 78 and a phalangeal component 79. The components 78 and 79 are positioned approximately at 90 degrees with respect to each other, thus illustrating the flexibility of the prosthesis of the present invention.

Figure 17:
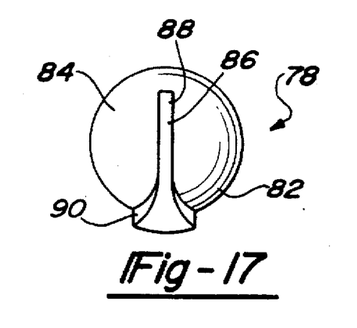
FIG. 17 is a side elevational view of the metacarpal component of the metacarpophalangeal component of FIG. 16.
Figure 18:
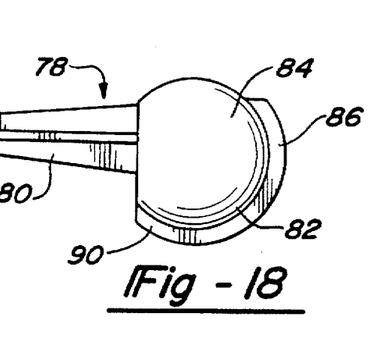
FIG. 18 is an end view of the metacarpal component shown in FIG. 17 according to the teachings of a preferred embodiment of the present invention.

With respect to FIGS. 17 and 18 in which side and end views of the metacarpal component 78 are shown respectively, the metacarpal component 78 according to the second preferred embodiment includes a stem portion 80 and a head portion 82. The stem portion 80 is preferably of the shape and finish of the stem portion 52 discussed above with respect to the first preferred embodiment. The head portion 82 includes a spherical head portion 84 having a flange 86 formed thereon. The flange 86 extends partially around the outer periphery of the head portion 84 and includes a narrow portion 88 and a tapered portion 90. The narrow portion 88 is defined by a relatively constant width while the tapered portion 90 is defined by a width that gradually increases from the narrow portion 88. The head portion 84 of the metacarpal component 78 is used to transfer load to the phalangeal component while the flange 86 is able to control radial and ulnar deviation also as described below.

Figure 19:
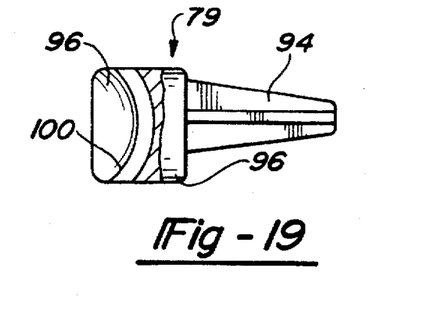
FIG. 19 is a side view shown in partial cross section of a phalangeal component of the present invention that mates with the metacarpal component shown in FIG. 17 according to a preferred embodiment of the present invention.
Figure 20:
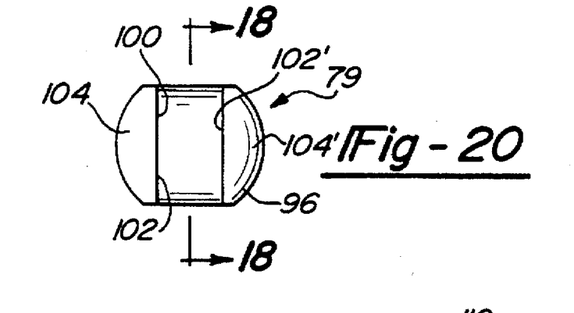
FIG. 20 is an end view of the phalangeal component shown in FIG. 19 according to a preferred embodiment of the present invention.

The phalangeal component 79 according to the second preferred embodiment of the present invention is shown in FIGS. 19 and 20 in which side and end views of the phalangeal component 79 are shown respectively. The phalangeal component 79 includes a stem portion 94 and a socket portion 96. The socket portion 96 has a curved channel 100 disposed therein which defines a pair of opposed walls 102 and 102'. The curved channel 100 is clearly seen in FIG. 19 as being a partially fragmented view taken along lines 18—18 of FIG. 20. The width of the channel 100 is approximately that of the widest point of the flange 86 on the metacarpal component 78. The socket portion 96 also includes a pair of spaced apart curved surfaces 104 and 104'. The surfaces 104 and 104' are dimensioned so as to closely mate with the spherical surface of the head portion 84. Accordingly, the load between the metacarpal component 78 and the phalangeal component 79 is able to be primarily transferred between the surfaces 104 and 104' of the phalangeal component 79 and the head portion 84 of the metacarpal component 78. In addition, because flange 86 of the metacarpal component 78 is tapered while the width of the channel 100 in the phalangeal component 79 is uniform, the relationship of the flange 86 with respect to the channel 100 is able to control radial and ulnar deviation.

The phalangeal component 79 is preferably formed from a two-piece construction as described above with respect to the phalangeal component 64. In addition, the stem portion 94 of the phalangeal component 64 is of a construction and finish that is similar to that of the stem portion 52 of the metacarpal component 50 of the first preferred embodiment.

The operation of the metacarpophalangeal prosthesis 77 according to the second preferred embodiment of the present invention will now be described. When the metacarpophalangeal prosthesis 77 is in full flexion as is shown in FIG. 16, the tapered portion 90 of the metacarpal component 78 is fully positioned within the channel 100. Accordingly, the widest part of the tapered portion 90 contacts the walls 102 and 102' of the channel 100 thereby preventing ulnar and radial deviation. As the phalangeal component 79 is moved from maximum flexion toward the neutral position, a gradually increasing amount of separation is provided between the widest part of the taper 90 and the walls 102 and 102' due to the configuration of the tapered portion 90. This increasing amount of separation is able to gradually increase the amount of radial and ulnar deviation permitted from 0 degrees at full flexion to approximately 15 degrees in the neutral position. In addition, because the narrow portion 88 of the flange 86 has a constant width, radial and ulnar deviation of approximately 15 degrees is permitted through extension.

Figure 21:
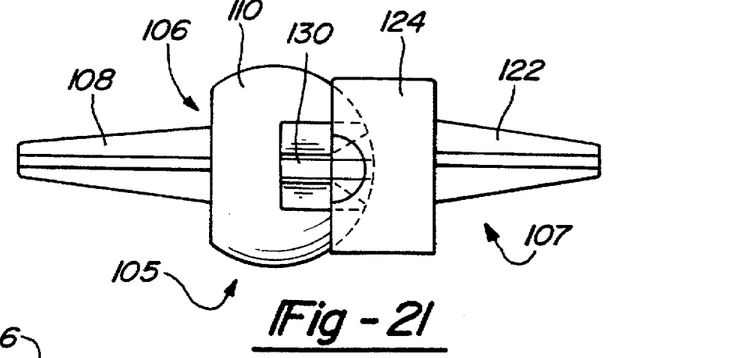
FIG. 21 is a top view of a metacarpophalangeal prosthesis according to the teachings of an additional alternate embodiment of the present invention.
Figure 22:
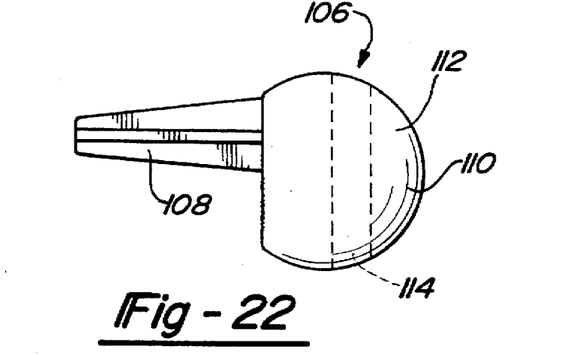
FIG. 22 is a side elevational view of the metacarpal component of the metacarpophalangeal prosthesis of FIG. 21.
Figure 23:
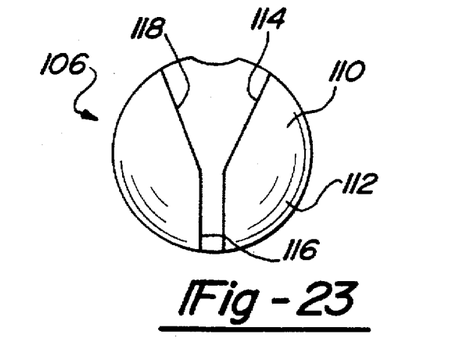
FIG. 23 is an end view of the metacarpal component shown in FIG. 22 according to the teachings of a preferred embodiment of the present invention.

The third preferred embodiment of the metacarpophalangeal prosthesis 30 of the present invention is shown in FIGS. 21 through 25 and will now be described. Referring to FIG. 21, a top plan view of a metacarpophalangeal prosthesis 105 is shown in neutral position and includes a metacarpal component 106 and a phalangeal component 107. As shown in FIGS. 22 and 23 in which side and end views of the metacarpal component 106 are shown respectively, the metacarpal component 106 includes a stem portion 108 and a head portion 110 which are integrally formed from a biocompatible material such as titanium, cobalt chrome, or ceramic. The stem portion 108 is preferably of the same construction and finish as the stem portion 52 discussed above. The head portion 110 includes a head portion 112 having a spherical outer surface with a channel 114 defined therein. The channel 114 includes a narrow portion 116 of constant width and a tapered portion 118 of varying width. The floor of the channel 114 is preferably flat as illustrated in broken lines shown in FIG. 22.

Figure 24:
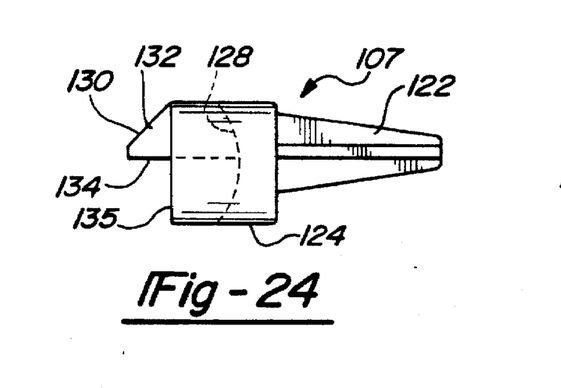
FIG. 24 is a side elevational view of the phalangeal component that mates with the metacarpal component of FIG. 22 according to the teachings of a preferred embodiment of the present invention.
Figure 25:
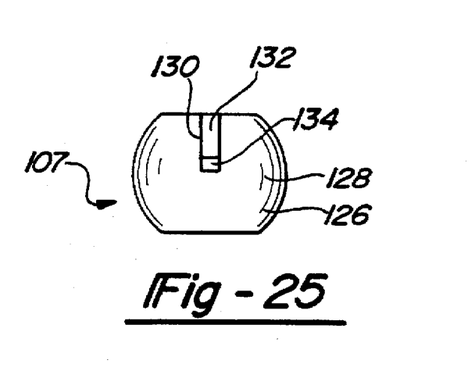
FIG. 25 is an end view of the phalangeal component shown in FIG. 24 according to the teachings of a preferred embodiment of the present invention.

As shown in FIGS. 24 and 25 in which side and end views of the phalangeal component 107 are shown respectively, the phalangeal component 107 according to the third preferred embodiment of the present invention includes a stem portion 122 and a socket portion 124. In addition, the stem portion 122 and the socket portion 124 are preferably formed from a metal and a plastic respectively, and the stem portion 122 is preferably of the construction and finish similar to that of the stem portion 52.

The socket portion 124 includes a spherical recessed area 128 having a curvature which is substantially the same as the spherical surface of the head portion 112. The recessed area 128 continuously rests against the spherical surface of the head portion 112 so as to be able to transfer the load between the metacarpal component 106 and the phalangeal component 107 throughout the range of flexion.

The socket portion 124 also includes a tab 130 which is integrally mated with, and extends outward from, the recessed area 128. The tab 130 has an angled surface 132 and a surface 134 which is generally perpendicular to the plane defined by an end 135. As illustrated in FIG. 21, the tab 130 fits within the channel 114 of the metacarpal component 106. When in the neutral and extension positions, the tab 130 is positioned within the tapered portion 118 of the channel 114 thereby allowing radial and ulnar deviation. The angled surface 132 of the tab 130 contacts the floor of the channel 114 when maximum extension occurs.

As the phalangeal component 107 is rotated with respect to the metacarpal component 106 toward the position of full flexion, the walls of the tapered portion 118 increasingly constrain the tab 130 until radial and ulnar deviation of the phalangeal component 107 with respect to the metacarpal component is fully constrained at full flexion. The full flexion is reached when the surface 134 of the tab 130 contacts the floor of the channel 114.

Figure 26:
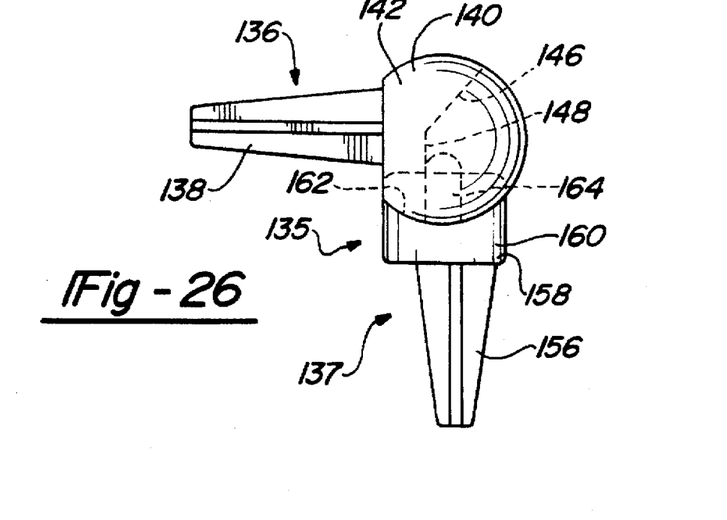
FIG. 26 is a side elevational view of a metacarpophalangeal prosthesis according to yet a further alternate embodiment of the present invention.
Figure 27:
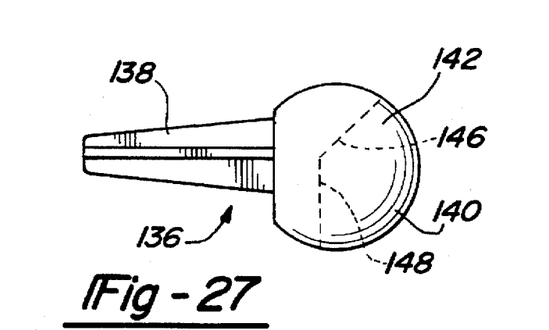
FIG. 27 is a side elevational view of the metacarpal component of the metacarpophalangeal prosthesis of FIG. 26.
Figure 28:
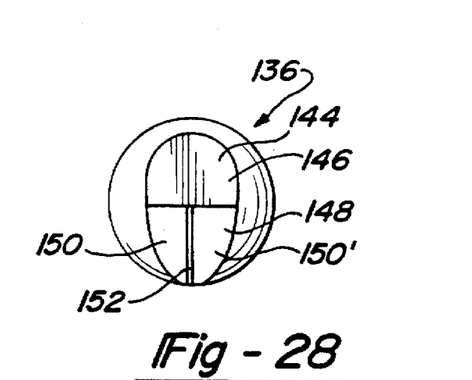
FIG. 28 is an end view of the metacarpal component of FIG. 27 according to a preferred embodiment of the present invention.

The fourth preferred embodiment of the present invention is shown in FIGS. 26 through 30 and will now be described. Referring to FIG. 26, a side view of a metacarpophalangeal prosthesis 135 is shown in flexion and includes a metacarpal component 136 and a phalangeal component 137. As shown in FIGS. 27 and 28 in which side and end views of the metacarpal component 136 are shown respectively, a metacarpal component 136 includes a stem portion 138 and a head portion 140. The stem portion 138 and the head portion 140 are preferably integrally formed and are made of a biocompatible metal such as Ti-4A1-6V. The head portion includes a spherical head portion 142 that has a groove 144 defined therein. The groove 144 (shown in broken lines in FIG. 27 and in solid lines in FIG. 28) defines an extension constraining portion 146 and a flexion restraining portion 148. The extension constraining portion 146 is defined by a continuous sloping surface, while the flexion restraining portion 148 is defined by a pair of walls 150 and 150' that intersect at a notch 152.

Figure 29:
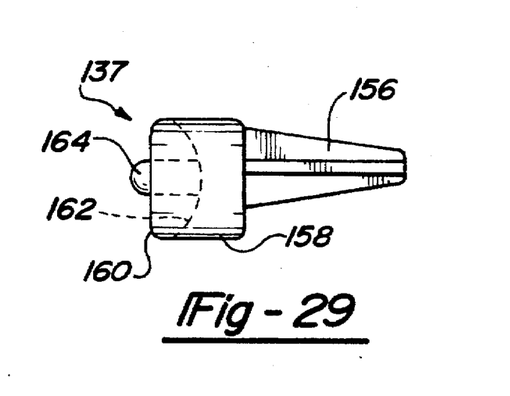
FIG. 29 is a side elevational view of the phalangeal component which is used with the metacarpal component shown in FIG. 27.
Figure 30:
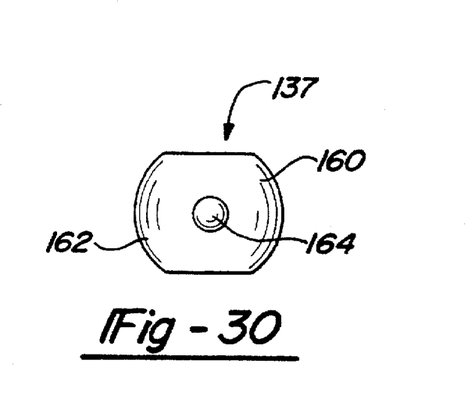
FIG. 30 is an end view of the phalangeal component shown in FIG. 29 according to the teachings of a preferred embodiment of the present invention.

The phalangeal component 137 according to the fourth preferred embodiment of the present invention includes a stem portion 156 and a socket portion 158 as shown in FIGS. 29 and 30 in which side and end views of the phalangeal component 137 are shown respectively. In a manner similar to that described above, the stem portion 156 and the socket portion 124 are preferably formed separately and then attached before implantation. In addition, the phalangeal component 137 is preferably composed of two materials such that the stem portion 156 is metal and the socket portion 158 is a plastic.

The socket portion 158 includes a recessed area 162 having a shape which corresponds to the spherical surface of the spherical head portion 142 of the metacarpal component 136. The recessed area 162 continuously rests against the spherical head portion 142 throughout the range of flexion so as to transfer load therebetween. The socket portion 158 further includes a pin 164 extends from the recessed area 162 and which is located in the groove 144 of the head portion 140 when the metacarpal component 136 is rotatably mated with the phalangeal component 137 as illustrated in FIG. 26.

When the phalangeal component 137 is in full flexion position as shown in FIG. 26, further movement is prevented as the pin 164 engages the wall of the flexion restraining portion 148. In addition, as shown in FIG. 28, the pin 164 rests within the notch 152 defined by the groove 144 such that the phalangeal component 137 is constrained against radial or ulnar deviation. As the phalangeal component 137 is moved from its position at full flexion toward the neutral position, the pin 164 is gradually moved from the notch 152 so as to allow an increasing amount of radial and ulnar deviation as the phalangeal component 137 approaches the neutral position. When maximum extension is achieved, the pin 164 contacts the extension constraining portion 146. However, unlike the constraint caused by the notch 152 of the flexion restraining portion 148, the curved continuous wall of the extension constraining portion 146 restricts further extension while still allowing radial and ulnar deviation to approximately 15 degrees.

From the preceding description of the preferred embodiments, it is evident that the objects of the invention are attained. Although the invention has been described and illustrated in detail, it is to be clearly understood that the same is intended by way of illustration and example only and is not to be taken by way of limitation. The spirit and scope of the invention are to be limited only by the terms of the appended claims.

What is claimed is:

1. A metacarpophalangeal prosthesis for replacing a natural joint between a metacarpal and a proximal phalanx, the metacarpophalangeal prosthesis being operable to flex and extend so as to define a range of motion, said metacarpophalangeal prosthesis comprising:

a metacarpal component having a head portion, said head portion being defined by a first dimension and a second dimension, said first and second dimensions being substantially orthogonal with respect to one another, said head portion having a shape, said shape being defined as a substantially flattened spheroid that is generally circular in said first dimension and is generally ovoid in said second dimension;

a phalangeal component having a socket portion matable with said head portion, said head portion and said socket portion being in substantially continuous contact with one another throughout the range of motion from flexion to extension; and means for substantially limiting radial and ulnar deviation between said phalangeal component and said metacarpal component as a position of maximum flexion is approached.

2. The metacarpophalangeal prosthesis of claim 1, wherein said means for substantially limiting radial and ulnar deviation comprises a pair of shoulders being formed on opposing sides of said head portion.

3. The metacarpophalangeal prosthesis of claim 2, wherein said means for substantially limiting radial and ulnar deviation includes a pair of surfaces disposed on said socket portion and engageable with said shoulders disposed on said head portion, at least one of said shoulders having a first side which is operable to substantially engage one of said surfaces of said socket portion when said phalangeal component is in a position of maximum flexion with respect to said metacarpal component.

4. The metacarpophalangeal prosthesis of claim 3, wherein said first side of said at least one shoulder includes a substantially flat portion and said one of said surfaces of said socket portion includes a substantially flat portion, said flat portions being in substantially full contact with each other when said phalangeal component is in said position of maximum flexion with respect to said metacarpal component.

5. The metacarpophalangeal prosthesis of claim 3, wherein said means for substantially limiting radial and ulnar deviation includes a pair of surfaces disposed on said socket portion and engageable with said shoulders disposed on said head portion, at least one of said shoulders having a side which is operable to substantially engage one of said surfaces of said socket portion when said phalangeal component is in a position of maximum extension with respect to said metacarpal component.

6. The metacarpophalangeal prosthesis of claim 3, wherein said means for substantially limiting radial and ulnar deviation includes a pair of surfaces disposed on said socket portion and engageable with said shoulders disposed on said head portion, at least one of said shoulders having a side which is operable to engage one of said surfaces of said socket portion in line contact.

7. The metacarpophalangeal prosthesis of claim 1, wherein said head portion of said metacarpal component defines a spherical surface, said means for substantially limiting radial and ulnar deviation further includes a flange formed on said spherical surface having an area of substantially constant width and an area of gradually increasing width.

8. The metacarpophalangeal prosthesis of claim 7, wherein said means for substantially limiting radial and ulnar deviation further includes a channel defined in said socket portion and being of constant width, said flange being positionable within said channel.

9. The metacarpophalangeal prosthesis of claim 1, wherein said head portion of said metacarpal component defines a spherical surface, said means for substantially limiting radial and ulnar deviation further includes a channel defined in said spherical surface having a region of constant width and a region of gradually increasing width.

10. The metacarpophalangeal prosthesis of claim 9, wherein said socket portion member further includes a recessed area and said means for substantially limiting radial and ulnar deviation further includes a tab extending from said recessed area, said tab being positionable within said channel.

11. The metacarpophalangeal prosthesis of claim 10, wherein said socket portion includes a recessed area and said means for substantially limiting radial and ulnar deviation further includes a pin extending from said recess area, said pin being positionable within said groove.

12. The metacarpophalangeal prosthesis of claim 1, wherein said head portion of said metacarpal component defines a spherical surface and said means for substantially limiting radial and ulnar deviation further includes a groove formed in said spherical surface, said groove having a curved portion and a notched portion defined by a pair of intersecting walls.

13. The metacarpophalangeal prosthesis of claim 1, wherein said head portion is composed of a first material and said socket portion is composed of a second material that is different from said first material, said first material being a metal and said second material being a plastic.

14. The metacarpophalangeal prosthesis of claim 1, where said phalangeal component is formed from a plastic.

15. The metacarpophalangeal prosthesis of claim 1, wherein each of said metacarpal and phalangeal components include a stem for anchoring said metacarpal and phalangeal components to the metacarpal and proximal phalanx respectively, at least one of said stems being cross-shape in cross section.

16. The metacarpophalangeal prosthesis of claim 1, wherein each of said metacarpal and phalangeal components are capable of being manipulated from between 90 degrees of angularity to 180 degrees of angularity with respect to one another.

17. The metacarpophalangeal prosthesis of claim 1, wherein said means for substantially limiting radial and ulnar deviation further prohibit rotation of said metacarpal component with respect to said phalangeal component.

18. A metacarpophalangeal prosthesis for replacing a natural joint between a metacarpal and a proximal phalanx, the metacarpophalangeal prosthesis being able to flex and extend so as to define a range of motion, said metacarpophalangeal prosthesis comprising:

a metacarpal component having a mating surface and a head portion, said head portion being defined by a first dimension and a second dimension, said first and second dimensions being substantially orthogonal with respect to one another, said head portion having a shape, said shape being defined as a substantially flattened spheroid that is generally circular in said first dimension and is generally ovoid in said second dimension;

a phalangeal component having a mating surface for rotatably mating with said mating surface of said metacarpal component, said phalangeal component being operable to transfer load to said metacarpal component primarily through the mating surface of said phalangeal component and said mating surface of said metacarpal component; and means for substantially limiting radial and ulnar deviation as said phalangeal component approaches said position of maximum flexion with respect to said metacarpal component.

19. The metacarpophalangeal prosthesis of claim 18, wherein said means for substantially limiting radial and ulnar deviation comprises a pair of shoulders being formed on said head portion.

20. The metacarpophalangeal prosthesis of claim 19, wherein said means for substantially limiting radial and ulnar deviation includes a pair of surfaces disposed on said socket portion and engageable with said shoulders disposed on said head portion, at least one of said shoulders having a first side which is operable to substantially engage one of said surfaces of said socket portion when said phalangeal component is in said position of maximum flexion with respect to said metacarpal component.

21. A metacarpophalangeal prosthesis for replacing a natural joint between a metacarpal and a proximal phalanx, the metacarpophalangeal prosthesis being able to flex and extend so as to define a range of motion between a first position and a second position, said metacarpophalangeal prosthesis comprising:

a metacarpal component having a head portion with a convex mating surface, said head portion being defined by a first dimension and a second dimension, said first and second dimensions being substantially orthogonal with respect to one another, said head portion having a shape, said shape being defined as a substantially flattened spheroid that is generally circular in said first dimension and is generally ovoid in said second dimension;

a phalangeal component having a socket portion with a concave mating surface substantially corresponding to said convex mating surface, said convex mating surface being rotatably mated with said concave mating surface, said phalangeal component being operable to transfer load to said metacarpal component primarily through said concave mating surface of said phalangeal component and said convex mating surface of said metacarpal component;

first means associated with said head portion for constraining radial and ulnar deviation as the prosthesis approaches the second position; and second means associated with said socket portion for constraining radial and ulnar deviation as the prosthesis approaches the second position;

whereby said concave mating surface contacts said convex mating surface between the first position and the second position.

22. The metacarpophalangeal prosthesis of claim 21, wherein said first means associated with said head portion for constraining radial and ulnar deviation comprises a pair of shoulders and wherein said second means associated with said socket portion for constraining radial and ulnar deviation comprises a pair of surfaces able to engage said shoulders, said pair of shoulders being formed on said head portion and said pair of surfaces being formed on said socket portion.

23. The metacarpophalangeal prosthesis of claim 22, wherein said shoulders define a right shoulder respectively and a left shoulder, and wherein each of said right and left shoulders has a first side and a second side and wherein said surfaces on said socket portion can substantially contact only one or the other of said first side of said right shoulder or said first side of said left shoulder when said phalangeal component is in the first position and wherein said surfaces substantially contact said second sides when said phalangeal component is in the second position.

* * * * *

UNITED STATES PATENT AND TRADEMARK OFFICE
CERTIFICATE OF CORRECTION

PATENT NO. : 5,674,297
DATED : October 7, 1997
INVENTOR(S) : Lewis B. Lane et al.

It is certified that error appears in the above-identified patent and that said Letters Patent is hereby corrected as shown below:

Column 5, line 23,          "designed" should be --designated--.
Column 14, line 31, Claim 23, delete "each of" after --wherein--.

Signed and Sealed this

Twenty-third Day of February, 1999

Attest:

Q. TODD DICKINSON

*Attesting Officer*      *Acting Commissioner of Patents and Trademarks*